United States Patent [19]

Bloch

[11] Patent Number: 5,272,256
[45] Date of Patent: Dec. 21, 1993

[54] NUCLEAR AUTOANTIGEN

[75] Inventor: Donald B. Bloch, Brookline, Mass.

[73] Assignee: The General Hospital Corporation, Boston, Mass.

[21] Appl. No.: 844,298

[22] Filed: Feb. 3, 1992

[51] Int. Cl.$^5$ .................. A61K 37/10; G01N 33/53; C07K 15/06; C07K 17/02
[52] U.S. Cl. .................. 530/358; 530/350; 530/403; 436/508; 935/71
[58] Field of Search ............... 530/350, 358, 403; 436/508

[56] References Cited

U.S. PATENT DOCUMENTS 4,784,942  11/1988  Harley .
4,870,161   9/1989  Spiegel ........................ 530/326

FOREIGN PATENT DOCUMENTS 0315254     5/1989  European Pat. Off. .
WO88/09932 12/1988  PCT Int'l Appl. .
WO91/11718  8/1991  PCT Int'l Appl. .

OTHER PUBLICATIONS

De Matteis et al, "Characterization of Calcium-triggered Secretion in Permeabilized Rat Basophilic Leukemia Cells" J. Biol. Chem. 266(16):10452–10460, 1991.
Neer et al, "Functions of G-Protein Subunits" Cold Spring Harbor Symposia on Quantitative Biology, vol. LIII, Cold Spring Harbor Laboratory, 1988, pp. 241–246.
Gilman A. G., "G Proteins: Transducers of Receptor-Generated Signals" Ann Rev Biochem 56:615–649, 1987.
Stryer et al, "G Proteins: A Family of Signal Transducers" Ann Rev Cell Biol 2:391–419, 1986.
Akizuki et al., The Jorunal of Clinical Investigation 59:264–272, 1977.
Borel et al., J. Clin Invest. 82:1901–1907, 1988.
Diner et al., The Journal of Immunology 122:1886–1891, 1979.
Golan et al., The Journal of Experimental Medicine 134:1046–1061, 1971.
Kelly, Textbook of Rheumatology 2nd edition, 667–694, 1985.
Jenkins et al., Journal of Experimental Medicine 165:302–319, 1987.
Quill et al., The Journal of Immunology 138:3704–3712, 1987.
Wells et al., Clin. Exp. Immunol. 38:424–435, 1979.
Wilkinson et al., The Journal of Immunology 139:326–331, 1987.
Vitetta et al., Science 238:1098–1104, 1987.

Primary Examiner—Christine M. Nucker
Assistant Examiner—Julie Krsek-Staples
Attorney, Agent, or Firm—Fish & Richardson

[57] ABSTRACT

The invention relates to a Ge protein having an apparent molecular weight of 170 kilodaltons when derived from HeLa cells. The Ge protein is a nuclear autoantigen that may be used to detect autoimmune disorders, such as Sjogren's syndrome, which is characterized by the presence of antinuclear antibodies binding to the Ge protein.

2 Claims, 9 Drawing Sheets

```
        gaattcggggcaggtcatctgtctctcaggagatgatagctccacctgcattgggatttg
  1     ---------+---------+---------+---------+---------+---------+  60
        cttaagccccgtccagtagacagagagtcctctactatcgaggtggacgtaaccctaaac

N  S  G  Q  V  I  C  L  S  G  D  D  S  S  T  C  I  G  I  W  - gccaaggagtgagattgtggctagcagtgactctagcatttcaagcaaggcccggggaag
  61    ---------+---------+---------+---------+---------+---------+ 120
        cggttcctcactctaacaccgatcgtcactgagatcgtaaagttcgttccgggcccttc

P  R  S  E  I  V  A  S  S  D  S  S  I  S  S  K  A  R  G  S  - caacaaggtgaaaattcagcctgtcgccaagtatgactgggaacagaagtactactatgg
  121   ---------+---------+---------+---------+---------+---------+ 180
        gttgttccactttttaagtcggacagcggttcatactgacccttgtcttcatgatgatacc

N  K  V  K  I  Q  P  V  A  K  Y  D  W  E  Q  K  Y  Y  Y| G  -

CaacctgattgctGTGTCTAACTCCTTCTTGGCCTATGCCATTCGGGCTGCCAACAATGg
  181   ---------+---------+---------+---------+---------+---------+ 240
        GttggactaacgaCACAGATTGAGGAAGAACCGGATACGGTAAGCCCGACGGTTGTTACc

N  L  I  A  V  S  N  S  F  L  A  Y  A  I  R  A  A  N  N  G  -

CTCTGCCATGGTGCGgGTGATCAGCGTCaGCaCTTCGGAGCGGACCTTGCTCAAGGgCTT
  241   ---------+---------+---------+---------+---------+---------+ 300
        GAGACGGTACCACGCcCACTAGTCGCAGtCGtGAAGCCTCGCCTGGAACGAGTTCCcGAA

S  A  M  V  R  V  I  S  V  S  T  S  E  R  T  L  L  K  G  F  -

CACAGGCAGTGTGGCTGATCTGGCTTTCGCGCACCTCAACTCTCCACAGCTGGCCTGCCT
  301   ---------+---------+---------+---------+---------+---------+ 360
        GTGTCCGTCACACCGACTAGACCGAAAGCGCGTGGAGTTGAGAGGTGTCGACCGGACGGA

T  G  S  V  A  D  L  A  F  A  H  L  N  S  P  Q  L  A  C  L  -

GGATgaggcaggcAACCTGTTCGTGTGGCGCTTGGCTcTGGTTAATGGCAAAATTCAAGA
  361   ---------+---------+---------+---------+---------+---------+ 420
        CCTActccgtccgTTGGACAAGCACACCGCGAACCGAgACCAATTACCGTTTTAAGTTCT

D  E  A  G  N  L  F  V  W  R  L  A  L  V  N  G  K  I  Q  E  -

AGAGATCTTGGTCCATATTCGGCAGCCAGAGGGCACGCCACTGAACCACTTTCGCAGGAT
  421   ---------+---------+---------+---------+---------+---------+ 480
        TCTCTAGAACCAGGTATAAGCCGTCGGTCTCCCGTGCGGTGACTTGGTGAAAGCGTCCTA

E  I  L  V  H  I  R  Q  P  E  G  T  P  L  N  H  F  R  R  I  -

CAtctggTGCCCCttCATCCcTGAGGAGAGCGAAGACTGCTGTGAGGAGAGCAGCCCAAC
  481   ---------+---------+---------+---------+---------+---------+ 540
        GTagaccACGGGGaaGTAGGgACTCCTCTCGCTTCTGACGACACTCCTCTCGTCGGGTTG

I  W  C  P  F  I  P  E  E  S  E  D  C  C  E  E  S  S  P  T  -

AGTGGCCCTGCTGCatgaagaccgggctgaggtgtgggacctggacatcgtccgctccag
```

FIG. 2A

```
     ----------+----------+----------+----------+----------+----------+
541                                                                    600
     TCACCGGGACGACGtacttctggcccgactccacaccctggacctgtagcaggcgaggtc

V  A  L  L  H  E  D  R  A  E  V  W  D  L  D  I  V  R  S  S  - ccacagtacctggcctgtggatgttagccagatcaagcagggcttcattgtggtaaaagg
     ----------+----------+----------+----------+----------+----------+
601                                                                    660
     ggtgtcatggaccggacacctacaatcggtctagttcgtcccgaagtaacaccattttcc

H  S  T  W  P  V  D  V  S  Q  I  K  Q  G  F  I  V  V  K  G  - tcatagcacgtgcctcagtgaaggagccctctcctgatgggactgtgctggctactgc
     ----------+----------+----------+----------+----------+----------+
661                                                                    720
     agtatcgtgcacggagtcacttcctcgggagagaggactaccctgacacgaccgatgacg

H  S  T  C  L  S  E  G  A  L  S  P  D  G  T  V  L  A  T  A  - gagccacgatggctatgtcaagttctggcagatctacattgaggggcaagatgagccaag
     ----------+----------+----------+----------+----------+----------+
721                                                                    780
     ctcggtgctaccgatacagttcaagaccgtctagatgtaactccccgttctactcggttc

S  H  D  G  Y  V  K  F  W  Q  I  Y  I  E  G  Q  D  E  P  R  - gtgtctgcacgagtggaaacctcatgatgggcggcccctctcctgcctcctgttctgtga
     ----------+----------+----------+----------+----------+----------+
781                                                                    840
     cacagacgtgctcacctttggagtactacccgccggggagaggacggaggacaagacact

C  L  H  E  W  K  P  H  D  G  R  P  L  S  C  L  L  F  C  D  - caaccataagaaacaagaccctgatgtccctttctggaggttccttattactggtgctga
     ----------+----------+----------+----------+----------+----------+
841                                                                    900
     gttggtattctttgttctgggactacagggaaagacctccaaggaataatgaccacgact

N  H  K  K  Q  D  P  D  V  P  F  W  R  F  L  I  T  G  A  D  - ccagaaccgagagttaaagatgtggtgtacagtatcctggacctgcctgcagactattcg
     ----------+----------+----------+----------+----------+----------+
901                                                                    960
     ggtcttggctctcaatttctacaccacatgtcataggacctggacggacgtctgataagc

Q  N  R  E  L  K  M  W  C  T  V  S  W  T  C  L  Q  T  I  R  - cttctccccagatatcttcagctcagtgagtgtgcccccctagcctcaaggtttgcttgga
     ----------+----------+----------+----------+----------+----------+
961                                                                    1020
     gaagaggggtctatagaagtcgagtcactcacacggggatcggagttccaaacgaacct

F  S  P  D  I  F  S  S  V  S  V  P  P  S  L  K  V  C  L  D  - cctctcagcagaatacctgattctcagcgatgtgcaacggaaggtcctctatgtgatgga
     ----------+----------+----------+----------+----------+----------+
1021                                                                   1080
     ggagagtcgtcttatggactaagagtcgctacacgttgccttccaggagatacactacct

L  S  A  E  Y  L  I  L  S  D  V  Q  R  K  V  L  Y  V  M  E  - gctgctgcaaaaccaggaggagggCcacgcctgcttcagctccatctcggagttcctgct
     ----------+----------+----------+----------+----------+----------+
1081                                                                   1140
     cgacgacgttttggtcctcctcccGgtgcggacgaagtcgaggtagagcctcaaggacga

L  L  Q  N  Q  E  E  G  H  A  C  F  S  S  I  S  E  F  L  L  - cacccaccctgtgctgagctttggtatccaggttgtgagtcgctgccggctacggcacac
     ----------+----------+----------+----------+----------+----------+
1141                                                                   1200
     gtgggtgggacacgactcgaaaccataggtccaacactcagcgacggccgatgccgtgtg
```

FIG. 2B

```
          T  H  P  V  L  S  F  G  I  Q  V  V  S  R  C  R  L  R  H  T  -
     tgaggtgctgcctgccgaagaggaaaatgacagcctgggtgctgatggtacccatggagc
1201 ------------+---------+---------+---------+---------+---------+ 1260
     actccacgacggacggcttctccttttactgtcggacccacgactaccatgggtacctcg E  V  L  P  A  E  E  E  N  D  S  L  G  A  D  G  T  H  G  A  -
     cggtgccatggagtctgcggccggtgtgctcatcaagctcttttgtgtgcatactaaggc
1261 ------------+---------+---------+---------+---------+---------+ 1320
     gccacggtacctcagacgccggccacacgagtagttcgagaaaacacacgtatgattccg G  A  M  E  S  A  A  G  V  L  I  K  L  F  C  V  H  T  K  A  -
     actgcaagatgtgcagatCcgcttccagccacagctgaaccctgatgtggtggccccact
1321 ------------+---------+---------+---------+---------+---------+ 1380
     tgacgttctacacgtctaGgcgaaggtcggtgtcgacttgggactacaccaccggggtga L  Q  D  V  Q  I  R  F  Q  P  Q  L  N  P  D  V  V  A  P  L  -
     ggggacccacactgcccacgaggacttcacatttggagagtctcggcccgaactgggctc
1381 ------------+---------+---------+---------+---------+---------+ 1440
     cccctgggtgtgacgggtgctcctgaagtgtaaacctctcagagccgggcttgacccgag G  T  H  T  A  H  E  D  F  T  F  G  E  S  R  P  E  L  G  S  -
     tgagggcctggggtcagccgctcacggctcccagcctgacctccgacgaatcgtggagct
1441 ------------+---------+---------+---------+---------+---------+ 1500
     actcccggaccccagtcggcgagtgccgagggtcggactggaggctgcttagcacctcga E  G  L  G  S  A  A  H  G  S  Q  P  D  L  R  R  I  V  E  L  -
     gcctgcacctgccgacttcctcagtctgagcagtgagaccaagcccaagtTgatGACACC
1501 ------------+---------+---------+---------+---------+---------+ 1560
     cggacgtggacggctgaaggagtcagactcgtcactctggttcgggttcaActaCTGTGG P  A  P  A  D  F  L  S  L  S  S  E  T  K  P  K  L  M  T  P  -
     TGACGCCTTCATGACACCTAGCGCCTCCTTGCAGCagatcactgcctctcccagcagcag
1561 ------------+---------+---------+---------+---------+---------+ 1620
     ACTGCGGAAGTACTGTGGATCGCGGAGGAACGTCGtctagtgacggagagggtcgtcgtc D  A  F  M  T  P  S  A  S  L  Q  Q  I  T  A  S  P  S  S  S  -
     cagcagcggtagcagcagcagcagcagtagcagcagctcccttacagctgtgtctgc
1621 ------------+---------+---------+---------+---------+---------+ 1680
     gtcgtcgccatcgtcgtcgtcgtcgtcatcgtcgtcgagggaatgtcgacacagacg S  S  G  S  S  S  S  S  S  S  S  S  S  L  T  A  V  S  A  -
     catgagcagcacctcagctgtggacccctccttgaccaggccacctgaggagctgacctt
1681 ------------+---------+---------+---------+---------+---------+ 1740
     gtactcgtcgtggagtcgacacctggggaggaactggtccggtggactcctcgactggaa M  S  S  T  S  A  V  D  P  S  L  T  R  P  P  E  E  L  T  L  -
     gagccccaagctgcagctggatggcagcctgacaatgagcagcagtggcagccttcagGc
1741 ------------+---------+---------+---------+---------+---------+ 1800
     ctcggggttcgacgtcgacctaccgtcggactgttactcgtcgtcaccgtcggaagtcCg

```
     aagcccgcgtGgcctcctgcctggcctgctcccagcccagctgacaaactgactcccaa
1801 ------------+---------+---------+---------+---------+---------+ 1860
     ttcgggcgcaCcggaggacggaccggacgagggtcggggtcgactgtttgactgagggtt

S  P  R  G  L  L  P  G  L  L  P  A  P  A  D  K  L  T  P  K  - ggggccgggccaggtgcctactgccacctctgcactgtccctggagctgcaggaagtgga
1861 ------------+---------+---------+---------+---------+---------+ 1920
     ccccggcccggtccacggatgacggtggagacgtgacagggacctcgacgtccttcacct

G  P  G  Q  V  P  T  A  T  S  A  L  S  L  E  L  Q  E  V  E  - gcCCctggggctaccccaagcctcccctagccgcactcgttcccctgatgtcatctcctc
1921 ------------+---------+---------+---------+---------+---------+ 1980
     cgGGgaccccgatggggttcggaggggatcggcgtgagcaaggggactacagtagaggag

P  L  G  L  P  Q  A  S  P  S  R  T  R  S  P  D  V  I  S  S  - agcttccactgacctgtcccaggacatccctgagattgcatctgaggccctgtcccgtgg
1981 ------------+---------+---------+---------+---------+---------+ 2040
     tcgaaggtgactggacagggtcctgtagggactctaacgtagactccgggacagggcacc

A  S  T  D  L  S  Q  D  I  P  E  I  A  S  E  A  L  S  R  G  - ttttggctcctctgcaccagagggccttgagccagacagtatggcttcagccgcctcggc
2041 ------------+---------+---------+---------+---------+---------+ 2100
     aaaaccgaggagacgtggtctcccggaactcggtctgtcataccgaagtcggcggagccg

F  G  S  S  A  P  E  G  L  E  P  D  S  M  A  S  A  A  S  A  - actgcacctgctgtccccacggccccggCcaggGcccgagctcggcCCCCAGcTCGgGCT
2101 ------------+---------+---------+---------+---------+---------+ 2160
     tgacgtggacgacaggggtgccggggccGgtccCgggctcgagccgGGGGTCgAGCcCGA

L  H  L  L  S  P  R  P  R  P  G  P  E  L  G  P  Q  L  G  L  -

TGATGgAGgcCCTGggGATGgAGATCGgCATAaTAcCCCTCCCTCCTGGAGGCAGCCTT
2161 ------------+---------+---------+---------+---------+---------+ 2220
     ACTACcTCcgGGACcCCTACcTCTAGCcGTATtATgGGGAGGGAGGACCTCCGTCGGAA

D  G  P  G  D  G  D  R  H  N  T  P  S  L  L  E  A  A  L  -

GACCCAGGAGGCCTCGACTCCTGACAGTCAGGTTTGGCCCACAGCACCTGACATTACTCG
2221 ------------+---------+---------+---------+---------+---------+ 2280
     CTGGGTCCTCCGGAGCTGAGGACTGTCAGTCCAAACCGGGTGTCGTGGACTGTAATGAGC

T  Q  E  A  S  T  P  D  S  Q  V  W  P  T  A  P  D  I  T  R  -

TGAGACCTGCAGCACCCTGGCAGAAAGCCCCAGGAATGGCCTTCAGGAAAAGCACAAGAG
2281 ------------+---------+---------+---------+---------+---------+ 2340
     ACTCTGGACGTCGTGGGACCGTCTTTCGGGGTCCTTACCGGAAGTCCTTTTCGTGTTCTC

E  T  C  S  T  L  A  E  S  P  R  N  G  L  Q  E  K  H  K  S  -

CCTGGCCTTCCacCGACCACCATATCACCTGCTGCAGCAACGtGACAGCCAGGATGCCAG
2341 ------------+---------+---------+---------+---------+---------+ 2400
     GGACCGGAAGGtgGCTGGTGGTATAGTGGACGACGTCGTTGCaCTGTCGGTCCTACGGTC

L  A  F  H  R  P  P  Y  H  L  L  Q  Q  R  D  S  Q  D  A  S  -

TGCTGAGCAAAGTGACCATGATGATGAGGTGGCCAGCCTTGCCTCTGCTTCAGGAGGCTT
```

FIG. 2D

```
2401 ----------+----------+----------+----------+----------+----------+ 2460
     ACGACTCGTTTCACTGGTACTACTACTCCACCGGTCGGAACGGAGACGAAGTCCTCCGAA

A  E  Q  S  D  H  D  D  E  V  A  S  L  A  S  A  S  G  G  F  -

TGGCACCAAAGTTCCTGCTCCACGGCTGCCTGCCAaGGaCTGGAAGACCAAGGGATCCCC
2461 ----------+----------+----------+----------+----------+----------+ 2520
     ACCGTGGTTTCAAGGACGAGGTGCCGACGGACGGTtCCtGACCTTCTGGTTCCCTAGGGG

G  T  K  V  P  A  P  R  L  P  A  K  D  W  K  T  K  G  S  P  -

TCGAACCTCACCCAAGCTCAAGAGGAAAAGCAAGAAGGATGATGGGGATGCAGCCATGGG
2521 ----------+----------+----------+----------+----------+----------+ 2580
     AGCTTGGAGTGGGTTCGAGTTCTCCTTTTCGTTCTTCCTACTACCCCTACGTCGGTACCC

R  T  S  P  K  L  K  R  K  S  K  K  D  D  G  D  A  A  M  G  -

ATCCGGCTCACAGAGCACCAGGTGGCAGAGCCCCCTGAGGACTGGCCAGCACTAATTTG
2581 ----------+----------+----------+----------+----------+----------+ 2640
     TAGGGCCGAGTGTCTCGTGGTCCACCGTCTCGGGGGACTCCTGACCGGTCGTGATTAAAC

S  R  L  T  E  H  Q  V  A  E  P  P  E  D  W  P  A  L  I  W  -

GCAACAGCAGAGAGAGCTGGCAGAGCTGCGGCACAGCCAGGAAGAGCTGCTGCAGCGTCT
2641 ----------+----------+----------+----------+----------+----------+ 2700
     CGTTGTCGTCTCTCTCGACCGTCTCGACGCCGTGTCGGTCCTTCTCGACGACGTCGCAGA

Q  Q  Q  R  E  L  A  E  L  R  H  S  Q  E  E  L  L  Q  R  L  -

GTGTACCCAACTCGAAGGCCTGCAGAGCACAGTCACAGGCCACGTAGAACGTGCCCTTGA
2701 ----------+----------+----------+----------+----------+----------+ 2760
     CACATGGGTTGAGCTTCCGGACGTCTCGTGTCAGTGTCCGGTGCATCTTGCACGGGAACT

C  T  Q  L  E  G  L  Q  S  T  V  T  G  H  V  E  R  A  L  E  -

GACTCGGCACGAGCAGGAACAGCGGCGGCTGGAGCGAGCACTGGCTGAGGGGCAGCAGCG
2761 ----------+----------+----------+----------+----------+----------+ 2820
     CTGAGCCGTGCTCGTCCTTGTCGCCGCCGACCTCGCTCGTGACCGACTCCCCGTCGTCGC

T  R  H  E  Q  E  Q  R  R  L  E  R  A  L  A  E  G  Q  Q  R  -

GGGAGGGCACTGGCAGGAGCAGCTGACACAACAGTTGTCCCAAGCACTGTCGTCAGCTGT
2821 ----------+----------+----------+----------+----------+----------+ 2880
     CCCTCCCGTGACCGTCCTCGTCGACTGTGTTGTCAACAGGGTTCGTGACAGCAGTCGACA

G  G  H  W  Q  E  Q  L  T  Q  Q  L  S  Q  A  L  S  S  A  V  -

AGCTGGGCGGCTAGAGCGCAGCATACGGGATGAGATCAAGAAGACAGTCCCTCCATGTGT
2881 ----------+----------+----------+----------+----------+----------+ 2940
     TCGACCCGCCGATCTCGCGTCGTATGCCCTACTCTAGTTCTTCTGTCAGGGAGGTACACA

A  G  R  L  E  R  S  I  R  D  E  I  K  K  T  V  P  P  C  V  -

CTCAAGGAGTCTGGAGGCTATGGCAGGCCAACTGAGCAACTCAGTGGCTACCAAGCTCAC
2941 ----------+----------+----------+----------+----------+----------+ 3000
     GAGTTCCTCAGACCTCCGATACCGTCCGGTTGACTCGTTGAGTCACCGATGGTTCGAGTG

S  R  S  L  E  A  M  A  G  Q  L  S  N  S  V  A  T  K  L  T  -

AGCTGTGGAGGGCAGCATGAAAGAGAACATCTCCAAGCTGCTCAAGTCCAAGAACTTGAC
3001 ----------+----------+----------+----------+----------+----------+ 3060
     TCGACACCTCCCGTCGTACTTTCTCTTGTAGAGGTTCGACGAGTTCAGGTTCTTGAACTG
```

FIG. 2E

```
              A  V  E  G  S  M  K  E  N  I  S  K  L  L  K  S  K  N  L  T  -
       TGATGCCATCGCCCGAGCAGCTGCAGACACATTACAAGGGCCGATGCAGGCTGCCTACCG
3061   ---------+---------+---------+---------+---------+---------+   3120
       ACTACGGTAGCGGGCTCGTCGACGTCTGTGTAATGTTCCCGGCTACGTCCGACGGATGGC

D  A  I  A  R  A  A  A  D  T  L  Q  G  P  M  Q  A  A  Y  R  -
       GGAAGCCTTCCAGAGTGTGGTGCTGCCGGCCTTTGAGAAGAGCTGCCAGGCCATGTTCCA
3121   ---------+---------+---------+---------+---------+---------+   3180
       CCTTCGGAAGGTCTCACACCACGACGGCCGGAAACTCTTCTCGACGGTCCGGTACAAGGT

E  A  F  Q  S  V  V  L  P  A  F  E  K  S  C  Q  A  M  F  Q  -
       GCAAATCAATGATAGCTTCCGGCTGGGGACACAGGAATACTTGCAGCAGCTAGAAAGCCA
3181   ---------+---------+---------+---------+---------+---------+   3240
       CGTTTAGTTACTATCGAAGGCCGACCCCTGTGTCCTTATGAACGTCGTCGATCTTTCGGT

Q  I  N  D  S  F  R  L  G  T  Q  E  Y  L  Q  Q  L  E  S  H  -
       CATGAAGAGCCGGAACGGACGGGAACAGGAGGCCAGGGAGCCTGTGCTAGCCCAGCTGCG
3241   ---------+---------+---------+---------+---------+---------+   3300
       GTACTTCTCGGCCTTGCCTGCCCTTGTCCTCCGGTCCCTCGGACACGATCGGGTCGACGC

M  K  S  R  N  G  R  E  Q  E  A  R  E  P  V  L  A  Q  L  R  -
       GGGCCTGGTCAGCACACTGCAGAGTGCCACTGAGCAGATGCAGCCAcCGTGGCCGGCAGT
3301   ---------+---------+---------+---------+---------+---------+   3360
       CCCGGACCAGTCGTGTGACGTCTCACGGTGACTCGTCTACGTCGGTgGCACCGGCCGTCA

G  L  V  S  T  L  Q  S  A  T  E  Q  M  Q  P  P  W  P  A  V  -
       GuTCGTGCTgAGGTgCAGCACCAGCTGCATGTGGCTGTGGGCAGCCTGCAGGAGTCCATT
3361   ---------+---------+---------+---------+---------+---------+   3420
       CAAGCACGACTCCAcGTCGTGGTCGACGTACACCGACACCCGTCGGACGTCCTCAGGTAA

F  V  L  R  C  S  T  S  C  M  W  L  W  A  A  C  R  S  P  F  -
       TTAGCACAGGTACAGCGCATCGTTAAGGGTGAGGTGAGTGTGGCGCTCAAGGAGCAGCAG
3421   ---------+---------+---------+---------+---------+---------+   3480
       AATCGTGTCCATGTCGCGTAGCAATTCCCACTCCACTCACACCGCGAGTTCCTCGTCGTC

*  H  R  Y  S  A  S  L  R  V  R  *
       GCCGCCGTCACCTCCAGCATCATGCAGGCCATGCGCTCAGCTGCTGGCACACCTGTACCC
3481   ---------+---------+---------+---------+---------+---------+   3540
       CGGCGGCAGTGGAGGTCGTAGTACGTCCGGTACGCGAGTCGACGACCGTGTGGACATGGG

TCTGCCCACCTTGACTGCCAGGCCCAGCAAGCCCATATCCTGCAGCTGCTGCAGCAGGGC
3541   ---------+---------+---------+---------+---------+---------+   3600
       AGACGGGTGGAACTGACGGTCCGGGTCGTTCGGGTATAGGACGTCGACGACGTCGTCCCG

CACCTCAATCAGGCCTTCCAGCAGGCGCTGACAGCTGCTGACCTGAACCTGGTGCTGTAT
3601   ---------+---------+---------+---------+---------+---------+   3660
       GTGGAGTTAGTCCGGAAGGTCGTCCGCGACTGTCGACGACTGGACTTGGACCACGACATA
```

FIG. 2F

```
       GTGTGTGAAACTGTGGACCCAGCCCAGGTTTTTGGGCAGCCACCCTGCCCGCTCTCCCAG
3661   ------------------------------------------------------------+  3720
       CACACACTTTGACACCTGGGTCGGGTCCAAAAACCCGTCGGTGGGACGGGCGAGAGGGTC

CCTGTGCTCCTTTCCCTCATCCAGCAGCTGGCATCTGACCTTGGCACTCGAACTGACCTC
3721   ------------------------------------------------------------+  3780
       GGACACGAGGAAAGGGAGTAGGTCGTCGACCGTAGACTGGAACCGTGAGCTTGACTGGAG

AAGCTCAGCTACCTGGAAGAGGCCGTGATGCACCTGGACCACAGTGACCCCATCACTCGG
3781   ------------------------------------------------------------+  3840
       TTCGAGTCGATGGACCTTCTCCGGCACTACGTGGACCTGGTGTCACTGGGGTAGTGAGCC

GACCACATGGGCTCCGTTATGGCCCAGGTGCGCCAAAAGCTTTTTCAGTTCCTGCAGGCT
3841   ------------------------------------------------------------+  3900
       CTGGTGTACCCGAGGCAATACCGGGTCCACGCGGTTTTCGAAAAAGTCAAGGACGTCCGA

GAGcCACACAACTCACTTGGCAAAGCAGCTCGGCGTCTCAGCCTCATGCTGCATGGCCTC
3901   ------------------------------------------------------------+  3960
       CTCgGTGTGTTGAGTGAACCGTTTCGTCGAGCCGCAGAGTCGGAGTACGACGTACCGGAG

GTGACCCCCAGCCTCCCTTAGCTGCTAAGCCTGCCTTGCCCAGGGGTGGGATGGCACTGA
3961   ------------------------------------------------------------+  4020
       CACTGGGGGTCGGAGGGAATCGACGATTCGGACGGAACGGGTCCCCACCCTACCGTGACT

AGGCCAGCAGacaggccTAGGCTGGGGCAGGGTCACGGCTGGCCTTTACCTGCTCAGGCC
4021   ------------------------------------------------------------+  4080
       TCCGGTCGTCtgtccggATCCGACCCCGTCCCAGTGCCGACCGGAAATGGACGAGTCCGG CCATCTCTGGGGTGTTTGGGGGTCAGGGAGCAGGGAGCACTGGCCGTGGTCTACAGCGTG
4081   ------------------------------------------------------------+  4140
       GGTAGAGACCCCACAAACCCCCAGTCCCTCGTCCCTCGTGACCGGCACCAGATGTCGCAC TGGTAGTCAGAAGGTTTAGCTGGGCCCAGGGCAGGTATTGCGCCTGCTTGGGTTCTGCCA
4141   ------------------------------------------------------------+  4200
       ACCATCAGTCTTCCAAATCGACCCGGGTCCCGTCCATAACGCGGACGAACCCAAGACGGT TGCCTGGAGCATGACCCTGAGATCGTGACACCACTTGAGTGGAATTTTCCATGTTCCTTT
4201   ------------------------------------------------------------+  4260
       ACGGACCTCGTACTGGGACTCTAGCACTGTGGTGAACTCACCTTAAAAGGTACAAGGAAA

TTAGGTGTAATTTGGATCTTTTTGTTTTGAAAAACAT
```

FIG. 2G

```
4261 ---------+---------+---------+------- 4297
     AATCCACATTAAACCTAGAAAAACAAAACTTTTTGTA
```

NUCLEAR AUTOANTIGEN

BACKGROUND OF THE INVENTION

Autoimmune diseases are disorders in which an individual's immune system targets and destroys apparently normal tissue Autoimmune diseases include rheumatoid arthritis (RA), systemic lupus erythematosus (SLE), scleroderma (SCL), Sjogren's syndrome (SjS), polymyositis (PM), dermatomyositis (DM), mixed connective tissue disease (MCTD) and pemphigus vulgaris (PV). Autoantibodies are commonly directed against cellular proteins and nucleic acids. In certain diseases, such as PV, the target of autoantibodies is known and the autoantibody is thought to play a role in the pathogenesis of the disease. In other diseases, such as SLE, the target of many different autoantibodies have been identified but the role of autoantibodies in the pathogenesis of SLE is as yet uncertain.

Detection of autoantibodies in the serum of patients assists in the diagnosis of autoimmune diseases. Rheumatoid factor (IgM antibodies directed against human IgG) is detected in the majority of patients with RA and supports that diagnosis in a given individual (Kelly, W.N., et al. 1985. Textbook of Rheumatology. 2nd ed. Saunders. pp. 667). Antinuclear antibodies (ANA) are present in approximately 98% of individuals with active SLE. Although ANA are not specific for the diagnosis of SLE, the absence of these antibodies argues against the diagnosis of SLE in a given patient (Kelly et al., 1985 supra pp. 691).

Sjogren's syndrome (SjS) is an autoimmune disease characterized by a chronic inflammation and destruction of lacrimal and salivary glands that results in dry eyes and mouth. SjS may affect other organs including the lungs, kidneys, liver and central nervous system, and may be associated with vasculitis, cryoglobulinemia, increased incidence of lymphoma, and macroglobulinemia (Talal, N., 1988. *Primer in the Rheumatic Diseases*, 9th ed. Schumacher, R. H., eds. pp 136–138). The disease can occur in the absence of other connective tissue diseases ("primary" SjS) or can be associated with RA, SLE, SCL and PM ("secondary" SjS).

Up to 30% of patients with rheumatoid arthritis, 10% of patients with SLE, and 1% of patients with SCL have been reported as having secondary Sjogren's syndrome. Immunogenetic predisposition appears to play an important role in the incidence of Sjogren's syndrome.

ANA are detected in between 50 and 80% of patients with SjS. Antibodies directed against nucleoprotein antigen SS-B/La are also detected in many patients with SjS. Antibodies directed against SS-A/Ro are also detected in patients with this disorder (Talal, 1988, supra 136–138).

A diagnosis of Sjogren's syndrome is made when the triad of keratoconjunctivitis sicca, xerostomia, and mononuclear cell infiltration of the salivary gland is noted (Talal, 1988, suora pp. 136–138). This last finding is made by a lower lip biopsy. Treatment is geared toward symptomatic relief of mucosal dryness and meticulous oral hygiene, and includes artificial tears, ophthalmologic lubricating ointments, nasal sprays of normal saline, frequent sips of water, and oral fluoride treatments. There is currently no effective treatment for the ongoing exocrine gland destruction.

SUMMARY OF THE INVENTION

In one aspect, the invention features a substantially pure nucleic acid encoding a Ge protein polypeptide, or fragments thereof. In preferred embodiments, the nucleotide sequence of the nucleic acid is substantially as shown in FIG. 2 and SEQ ID NO: 1. In other preferred embodiments, the nucleic acid includes DNA encoding the amino acid residues shown in FIG. 2 and SEQ ID NO: 1; the nucleic acid may be included in a vector, preferably in a cell, most preferably in a cell that expresses the sequence of the nucleic acid.

In another aspect, the invention features an essentially homogeneous population of cells, each of which includes the sequence of a nucleic acid encoding the Ge protein polypeptide.

In yet another aspect, the invention features a method for manufacture of a Ge protein polypeptide. The method involves providing the cell that expresses a Ge protein polypeptide, e.g., the amino acid sequence of FIG. 2 (SEQ ID NO: 1), culturing the cell in a medium so as to express the sequence, and purifying a Ge protein polypeptide from the cell or the medium.

In another aspect, the invention includes a substantially pure preparation of a Ge protein polypeptide, preferably made by the method described above, or made by purification on an antibody affinity column. In preferred embodiments, the polypeptide has an apparent molecular weight of 170 kilodaltons when derived from HeLa cells.

In another aspect, the invention features a purified preparation of an antibody that binds to a substantially pure preparation of a Ge protein polypeptide.

In another aspect, the invention features a biologically active fragment of a Ge protein polypeptide. In preferred embodiments, the Ge protein polypeptide includes an amino acid sequence at least 90% homologous with the amino acid sequence of a naturally occurring Ge protein polypeptide.

In another aspect, the invention features a purified preparation of an antibody that binds to a biologically active fragment of a Ge protein polypeptide.

In another aspect, the invention features an affinity matrix including a Ge protein polypeptide or a biologically active fragment of a Ge protein polypeptide.

In another aspect, the invention features a method of detecting an autoimmune disorder, e g. an autoimmune disorder characterized by the presence of ANA, e.g. Sjogren's disease, in a mammal, e.g. in a human patient. The method involves providing a tissue sample from the patient, contacting the tissue sample with a Ge protein polypeptide, and detecting the formation of immune complexes between the Ge protein polypeptide and the sample, the formation of the complexes being correlated with a disease state, e.g. an autoimmune disorder, e.g., Sjogren's disease The method can also be used to detect a mammal, e.g., a human, at risk for an autoimmune disorder, e.g., an autoimmune disorder characterized by the presence of ANA, e.g., Sjogren's syndrome.

In another aspect, the invention features a method of detecting an autoimmune disorder, e.g. an autoimmune disorder characterized by the presence of ANA, e.g., Sjogren's disease, in a mammal, e.g., in a human patient. The method involves providing a tissue sample from the patient, contacting the tissue sample with a nuclear substrate, e.g., rat liver or Hep2, and detecting the formation of immune complexes between the substrate and the sample, the formation of a characteristic pattern, e.g., an atypical speckled pattern, being correlated with a disease state, e.g., Sjogren's disease. The method can also be used to detect a mammal, e.g., a human, at risk for an autoimmune disorder, e.g., an autoimmune disorder characterized by the presence of ANA, e.g., Sjogren's syndrome.

In another aspect, the invention features a method of detecting a viral infection in a human patient. The method involves providing a tissue sample from the patient, contacting the tissue sample with a Ge protein polypeptide, and detecting the formation of immune complexes between the Ge protein polypeptide and the sample, the formation of the complexes being correlated with a viral infection.

In another aspect, the invention features a method of preventing autoimmune disease, e.g., an autoimmune disease characterized by an ANA, in a mammal, e.g., in a human patient. The method involves administering an autoimmune-disease preventing amount of a Ge protein polypeptide to the patient. Preferably, the autoimmune disease is Sjogren's disease.

In another aspect, the invention features a method of treating an autoimmune disease, e.g., an autoimmune disease characterized by an ANA, in a mammal, e.g., in a human patient. The method involves administering an autoimmune disease tolerizing amount of a tolerogenic compound that includes a Ge polypeptide to said patient. Preferably, the autoimmune disease is Sjogren's disease.

The invention includes Ge protein polypeptides, e.g., Ge from any naturally occurring source and fragments of Ge that exhibit biological activity. Also included are homologous sequences; allelic variations; natural mutants; induced mutants; proteins encoded by DNA that hybridizes under high or low stringency conditions to Ge encoding nucleic acids retrieved from naturally occurring material; and polypeptides or proteins retrieved by antisera to Ge, especially by antisera to the active site or binding domain of Ge. The invention also provides for other polypeptides that include Ge polypeptides or biologically active-fragments thereof Peptides of the invention will generally exhibit at least about 70%, more preferably about 80%, more preferably 90%, and most preferably about 95% or even 99%, homology with all or part of a naturally occurring Ge amino acid sequence, e.g., with the sequence shown in FIG. 2. The length of comparison sequences will generally be at least about 8 amino acid residues, usually at least about 20 amino acid residues, more usually at least about 24 amino acid residues, typically at least about 28 amino acid residues, and preferably more than about 35 amino acid residues.

The present invention also provides for analogs of Ge. Analogs can differ from naturally occurring Ge by amino acid sequence differences or by modifications that do not affect sequence, or by both. Modifications include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes that affect glycosylation derived from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine. Analogs can differ from naturally occurring Ge by alterations of their primary sequence. These include genetic variants, both natural and induced. Induced mutants may be derived by various techniques, including random mutagenesis of the encoding nucleic acids using irradiation or exposure to ethanemethylsulfate (EMS), or may incorporate changes produced by site-specific mutagenesis or other techniques of molecular biology See, Sambrook, Fritsch and Maniatis (1989), *Molecular Cloning: A Laboratory Manual* (2d ed.), CSH Press, hereby incorporated by reference. Also included are analogs that include residues other than naturally occurring L-amino acids, e.g., D-amino acids or non-naturally occurring or synthetic amino acids, e.g., $\beta$ or $\gamma$ amino acids.

In addition to substantially full-length polypeptides, the present invention provides for biologically active fragments of the polypeptides. A Ge polypeptide (or fragment) is biologically active if it exhibits a biological activity of a naturally occurring Ge. Such biological activities include (1) the ability to bind an antibody preparation that produces the speckled nuclear staining pattern on Hep2 cells discussed below and shown in FIG. 1B, and (2) the ability to bind to an antibody that is directed at an epitope that is present on a naturally occurring Ge polypeptide.

Putative biologically active fragments of Ge polypeptides can be generated by methods known to those skilled in the art. The biological activities of a candidate fragment can be assessed by methods known to those skilled in the art, e.g., by methods described below.

The invention also includes nucleic acid sequences, and purified preparations thereof, that encode the Ge polypeptides described herein. The invention also includes antibodies, preferably monoclonal antibodies, that bind specifically to Ge polypeptides.

As used herein, the term "fragment", as applied to a polypeptide, will ordinarily be at least about 5 contiguous amino acids, typically at least about 10 contiguous amino acids, more typically at least about 20 contiguous amino acids, usually at least about 30 contiguous amino acids, preferably at least about 40 contiguous amino acids, more preferably at least about 50 contiguous amino acids, and most preferably at least about 60 to 80 or more contiguous amino acids in length.

As used herein, the term "substantially pure" describes a compound, e.g., a protein or polypeptide, e.g., a Ge protein or polypeptide, that has been separated from components that naturally accompany it. Typically, a compound is substantially pure when at least 10%, more preferably at least 20%, more preferably at least 50%, more preferably at least 60%, more preferably at least 75%, more preferably at least 90%, and most preferably at least 99%, of the total material (by volume, by wet or dry weight, or by mole per cent or mole fraction) in a sample is the compound of interest. Purity can be measured by any appropriate method, e.g., in the case of polypeptides by column chromatography, polyacrylamide gel electrophoresis, or HPLC analysis A compound, e.g., a protein, is also substantially purified when it is free of naturally associated components or when it is separated from the native contaminants that accompany it in its natural state.

A "substantially pure nucleic acid", as used herein, refers to a nucleic acid sequence, segment, or fragment that has been purified from the sequences that flank it in a naturally occurring state, e.g., a DNA fragment that has been removed from the sequences that are adjacent to the fragment, e.g., the sequences adjacent to the fragment in its normal site in the genome. The term also applies to nucleic acids that have been substantially purified from other components that naturally accompany the nucleic acid, e.g., RNA or DNA, that has been isolated from proteins that naturally accompany it in the cell.

"Homologous", as used herein, refers to the subunit sequence similarity between two polymeric molecules, e.g., between two nucleic acid molecules, e.g., two DNA molecules, or two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half, e.g., 5 of 10, of the positions in two compound sequences are homologous then the two sequences are 50% homologous, if 90% of the positions, e.g., 9 of 10, are matched or homologous the two sequences share 90% homology. By way of example, the DNA sequences 3'ATTGCC'5 and 3'TATGGC'5 share 50% homology.

"Tissue sample", as used herein, refers to any tissue sample that contains autoantibodies, e.g., whole blood, serum, plasma, pleural fluid, ascites fluid, or pericardial fluid.

"Nuclear substrate", as used herein, refers to a substrate which includes a Ge polypeptide, e.g., a slice of tissue which includes nucleated cells, e.g., a slice of rat liver. Preferably, the substrate is fixed so that characteristic distribution of Ge is obtained.

By "apparent molecular weight" is meant the molecular weight, determined on a denaturing polyacrylamide gel, by comparison with standards, e.g., protein standards, of known molecular weight.

The invention is useful for: identifying patients having antibodies to Ge; identifying patients having or at risk for an autoimmune disorder; identifying patients who have or are at risk for Sjogren's syndrome; identifying patients having a viral infection, most preferably an infection of a dsDNA virus such as Herpes or cytomegalovirus; treating disorders characterized by the presence of an antibody to the Ge protein; as a tool in the investigation of autoimmune disease; and as a tool in the investigation of nuclear localization.

Other features and advantages of the invention will be apparent from the following detailed description and from the claims.

BRIEF DESCRIPTION OF THE DRAWINGS

FIG. 2 (SEQ ID NO:1) is a representation of the partial nucleic acid sequence of a Ge protein-encoding cDNA (G6xt+178 bp) and the deduced partial amino acid sequence of the primary translation product (shown in one letter codon assignments).

DETAILED DESCRIPTION

Overview

Figure 1A:
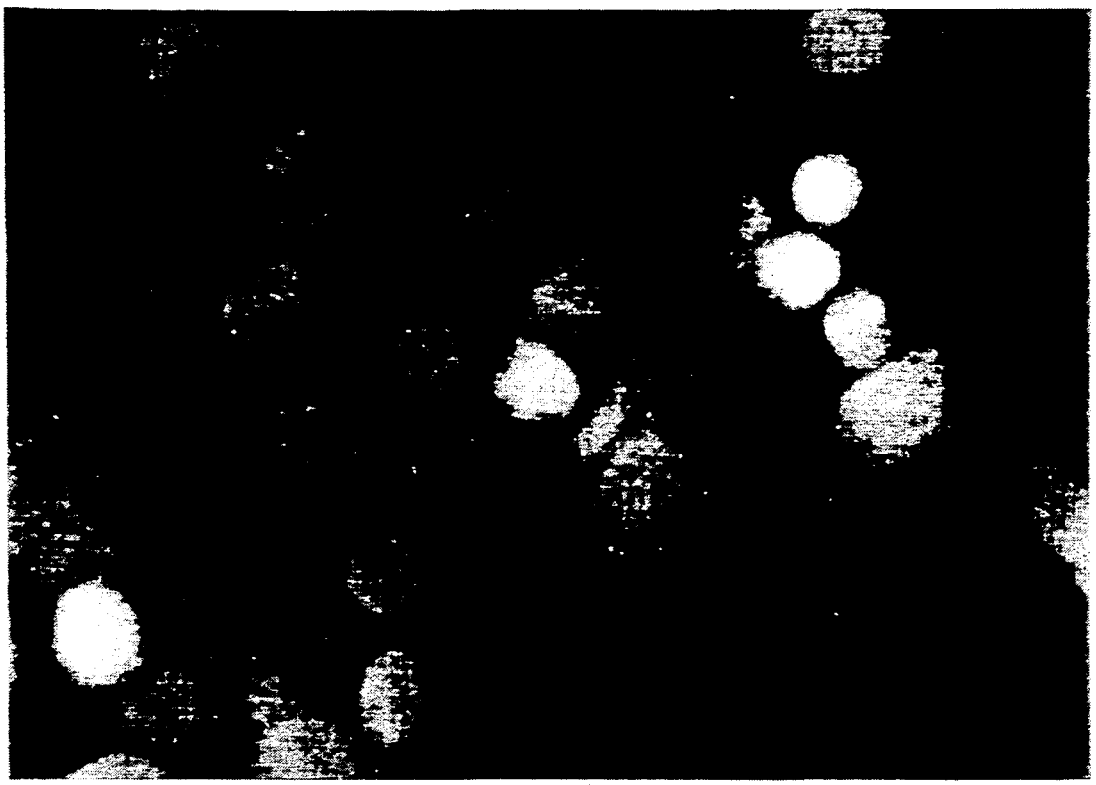
FIG. 1A is a photograph showing the atypical staining pattern produced by incubation of serum from a Sjogren's syndrome patient on Hep2 substrate.

Antinuclear antibodies have important roles in establishing the diagnosis and prognosis of certain autoimmune diseases. In addition, both the antibodies and their target antigens serve as powerful probes in molecular and cellular biology. The presence of specific autoantibodies in the serum of patients can identify a subgroup of patients who are at increased risk to develop certain complications associated with their autoimmune disease. In the course of a systematic study of serum samples yielding novel patterns of nuclear staining, it was observed that serum from a patient with Sjogren's syndrome produced an unusual speckled nuclear staining pattern on rat liver substrate. In addition, the serum produced a granular nuclear staining pattern and speckled cytoplasmic staining pattern using Hep2 substrate (FIG. 1A). The serum did not react with known autoantigens by immunodiffusion or ELISA. The serum did react with two polypeptides (70 and 170 kD) by immunoblot analysis.

To further characterize the cellular proteins identified by the patient's autoantibodies, serum was used to screen a λgtII expression library prepared from Hep2 cells. Three independent clones were identified. One of them, G6, is 1,269 bp long and the entire cDNA is part of an open reading frame. The nucleotide sequence of the G6 cDNA is shown (FIG. 2 (SEQ ID NO: 1), nucleotides 1381-2650). Sera from rats immunized with recombinant, partially purified protein translated from the G6 cDNA produced a nuclear speckled pattern on Hep2 substrate, and reacted with a 170 kD polypeptide in HeLa cells by immunoblot analysis.

The cDNA clone G6 was used to isolate a 4,118 bp cDNA and the polymerase chain reaction (PCR) was used to clone an additional 178 bp fragment at the 5' end of the cDNA. The resulting 4,297 nucleotide cDNA encodes nearly all of the 170 kD Ge polypeptide.

Constructs containing portions of the cDNA were used to map an epitope of the protein. A construct containing nucleotides 2,515–4,297 failed to react with the serum, whereas a construct containing 66 additional nucleotides did react with the serum. Thus the 22 amino acids encoded by these additional nucleotides must contribute to a critical epitope. This region contains part of the protein's putative nuclear localization region. These experiments are discussed in more detail below.

The indirect immunofluorescent test for ANA

ANA are detected in the serum of patents using an indirect immunofluorescence procedure that involves the use of rat liver substrate In this procedure, human serum is placed on a cryostat section of rat liver that permits attachment of immunoglobulin molecules with anti-nuclear specificity. The slide with the rat liver sections is washed with phosphate-buffered saline (PBS) and the fluorescein-conjugated goat anti-human IgG (Antibodies Inc.) is added. After washing again with PBS, the fluorescein-conjugated goat anti-human IgG is visualized by fluorescence microscopy. Serum samples are diluted with PBS; the highest titer that produces a positive test for ANA is reported to be the ANA titer.

The pattern of immunofluorescence often corresponds to a particular antigen against which the antibodies are directed. For example, a homogeneous pattern of immunofluorescence in the cell nucleus suggests the presence of antibodies directed against DNA or histone proteins. A speckled pattern is characteristic of antibodies directed against nRNP, Sm, Ro and La antigens. A rare pattern of immunofluorescence, termed "atypical speckled," is characterized by the presence of 5 to 100 discrete regions of nuclear fluorescence that are irregular in size and shape. This pattern differs from the "typical" speckled pattern in that the fluorescent regions are fewer in number and generally larger in size. The pattern is also distinguished from the "centromeric" pattern of immunofluorescence in which the stained regions are regular in size and shape, approximate in number to that of the chromosomes, and associated with the chromosomes of dividing cells.

Tests for antibodies directed against specific antigens

Antibodies directed against specific antigens may be detected using an Ouchterlony double diffusion assay or an enzyme-linked immunoabsorbent assay (ELISA). In double diffusion, a source of antigen and antibodies are placed in separate wells cut in agarose on the surface of a glass plate. The contents of both wells diffuse in all directions over time. Where antigen and specific antibodies meet, a precipitation line forms. ELISA involves coating a substrate, e.g., a well in a plastic dish, with a purified antigen and washing away nonadherent material. Serum to be tested is then added to the well. If present, antibodies attach to the antigen coating the well. Excess material is again washed away. An enzyme (such as horse radish peroxidase or alkaline phosphatase) coupled to a second antibody directed against human immunoglobulins is then added to the well and excess, nonadherent material is washed away. Finally the enzyme substrate is added to the well and a change in fluid color signifies the presence of enzyme (and therefore the second antibody and the first antibody).

Clinical presentation of a Sioqren's syndrome patient

The patient is a 75 year old woman with a long history of SjS characterized by dry eyes and dry mouth. The patient experienced numerous dental cares (resulting from loss of the protective effect of saliva) and episodes of parotiditis. A minor salivary gland biopsy in the past revealed lymphocytic infiltrate consistent with the diagnosis of SjS.

In 1988, the patient developed pulmonary complaints including chest pain and shortness of breath. Chest x-ray revealed pulmonary infiltrate. A lung biopsy in April, 1989 revealed evidence of chronic inflammation; infiltration of lung tissue by lymphocytes and plasma cells was detected These findings were considered consistent with SjS of the lung and the patient was treated with corticosteroids with resolution of her symptoms and radiographic abnormalities.

In Dec., 1990, the patient was noted to have. high titer ANA. The pattern of immunofluorescence on rat liver substrate was termed atypical. The serum did not react with nRNP, Ro, La, Sm, Jo-1, PCNA, and Scl-70 antigens. In addition, antibodies directed against other autoantigens, including Ku, PM-1 and Mi-1 have not been reported to produce the atypical pattern of immunofluorescence.

Immunoblot blot analysis using the patient's serum

To identify the target of autoantibodies in the patient's serum, the serum was used to probe an immunoblot prepared from a crude HeLa cell extract (Sambrook, J. et al. supra chapter 18). HeLa cells were scraped from tissue culture flasks and lysed using a loading buffer containing SDS, glycerol, and $\beta$-mercaptoethanol. Proteins were fractionated in an 8% SDS-polyacrylamide gel and transferred to nitrocellulose filters. Filters were treated with a tris-buffered saline containing non-fat dry milk (TBS/milk, 20 ml) to block nonspecific binding sites and then incubated overnight at 4° C. with the patients' serum diluted 1:1000 in 10 ml of TBS/milk. The filters were subsequently washed with TBS, treated with $^{125}$I-protein A (I $\mu$Ci, Amersham) for 1 hour at room temperature, and washed again with TBS. Two autoradiography.

Cloning of c-DNA encoding part of the 170 kD autoantigen

To further characterize the cellular proteins identified by the patient's autoantibodies, serum was used to screen a $\lambda$gt11 cDNA expression library prepared from a human hepatoma cell line, Hep2 (Clontech). Recombinant $\lambda$gt11 phages were plated on E. coli Yi090 and expression of the cDNA inserts fused to $\beta$-galactosidase was induced by overlaying nitrocellulose filters saturated with isopropylthiogalactopyranoside (IPTG) and incubating at 37° C. for four hours. Filters were treated with TBS/milk and then incubated overnight with the patient's serum diluted 1:100 in 40 ml of TBS/milk at 4° C (Sambrook, et al., supra chapter 12). Filters were then washed with TBS/milk and incubated with a 1:1000 dilution of S. aureus protein A linked to horseradish peroxidase (HRP; Boehringer Mannheim) in 20 ml of TBS/milk Filters were then washed and exposed to HRP substrate, 0-phenylenediamine.2HCl (Abbott Labs). Three positive clones were identified after screening approximately one million plaque forming units. One clone, G6, is 1269 base pairs long and contains a 423 amino acid partial open reading frame as determined by dideoxynucleotide sequencing. (See FIG. 2).

Partial cDNA G6 was ligated into expression vector pMAL (New England Biolabs) and used to transform competent MC1061 E. coli. Expression of recombinant protein fused to maltose binding protein (MBP) was induced using IPTG. The fusion protein was 110 kD as determined by SDS-polyacrilamide (8%) gel electrophoresis. The fusion protein reacted with antisera directed against MBP and with the patient's serum by immunoblot analysis.

Rat antisera directed against the G6/MBP fusion protein reproduced the atypical speckled pattern and reacted with a 170 kD protein in HeLa cells Recombinant protein was produced in E. coli and a crude bacterial lysate was fractionated by SDS-polyacrylamide gel electrophoresis (Sambrook, et al., supra chap. 17). Polyacrilamide containing proteins between 100 and 140 kD was excised from the gel. Proteins were extracted from the gel bands by grinding the gel in 2 ml of PBS and incubating on ice for 30 minutes. Remaining gel was separated from the fluid by centrifugation at 3000 rpm. The supernatant was emulsified in Freund's adjuvant. Three rats were immunized with recombinant protein and boosted on two occasions at two week intervals. Three control animals were immunized with an unrelated (maltose binding protein MBP-fusion protein of similar molecular weight. Sera from the animals were tested for the presence of ANA using Hep2 substrate and the indirect immunofluorescence procedure as described above, except that fluorescein-conjugated goat anti-rat IgG (Antibodies Inc.) was added in place of the anti-human IgG above. Fluoresceinated goat anti-rat IgG antisera was used to detect binding of rat immunoglobulin. Serum from the three rats immunized with G6/MBP contained antibodies that produced an atypical speckled pattern. Serum from the three control animals did not have ANA.

Serum from the rat with the highest titer ANA (1:400) was used to probe an immunoblot prepared using a crude HeLa cell extract, as described above. Rat immunoglobulin bound to the nitrocellulose filter was identified using $^{125}$I-goat anti-rat immunoglobulins (1 $\mu$Ci, Amersham). The serum contained antibodies that reacted with a 170 kD polypeptide.

Figure 1B:
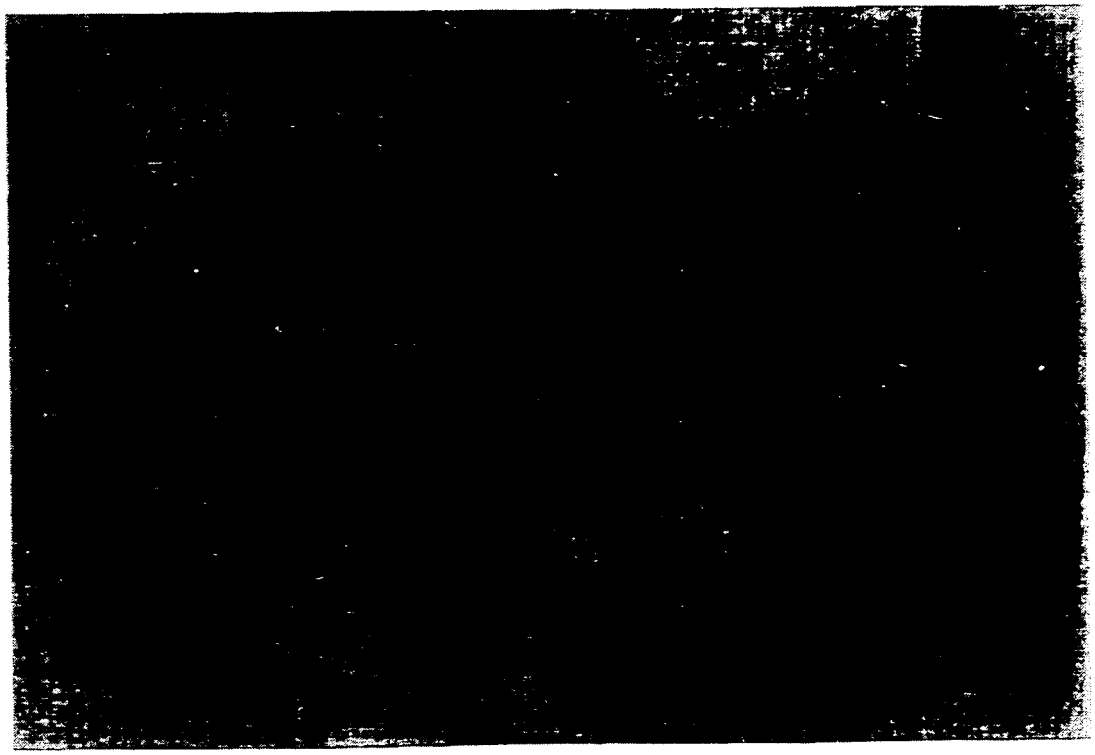
FIG. 1B is a photograph showing the atypical nuclear speckled staining pattern produced by rat antisera directed against Ge protein/maltose-binding-protein fusion protein.

These results demonstrated that the G6 cDNA encodes part of a protein that in HeLA cells is 170 kD in apparent molecular weight and that in Hep2 cells is nuclear in location. Antibodies to G6 polypeptide produce an atypical speckled pattern in the indirect immunofluorescent technique for the detection of ANA (FIG. 1B).

Cloning a nearly full length cDNA clone encoding the 170 kD autoantigen (Ge)

To obtain a full length cDNA encoding this autoantigen, cDNA G6 was radiolabeled using the technique of random priming (Sambrook, et al., Supra. chap. I0) and used to rescreen the human hepatoma cDNA library. Three additional cDNAs were obtained and purified by the technique of plaque purification. The longest of the three clones (G6xt) was 4118 bp in length and contained a 32411 bp open reading frame (FIG. 2, nucleotides 179–4297) The predicted primary amino acid sequence of this polypeptide was not found in the NCBI Blast Sequence Databax databank, which includes the GenBank, Genpept, Pir, and Swiss Prot databases An additional I78 bp of open reading frame at the 5' end of the cDNA was obtained by using the polymerase chain reaction (PCR) making use of DNA prepared from the human hepatoma cDNA library, a synthetic oligonucleotide primer corresponding to the "forward" λgt11 arm and a primer corresponding to the region at the 5' end of clone G6xt. The sequence of the G6xt cDNA (nucleotides 179–4297) and the additional 178 bp (nucleotides 1–178) is shown in FIG. 2.

The remaining 5' nucleotides will be obtained from a genomic clone that has been isolated by screening a human genomic library (Clontech) using radiolabeled I78 bp cDNA obtained by PCR amplication.

Mapping an epitope on autoantigen Ge.

Figures 2H, 3:
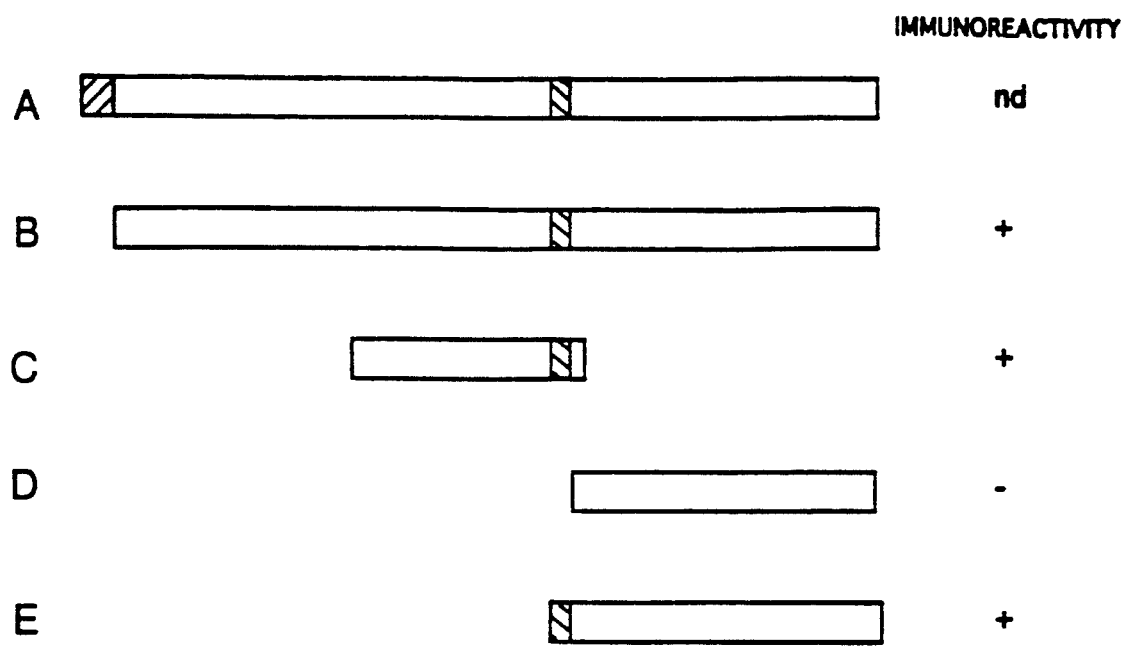
FIG. 3 is a representation of fragments of cDNA G6xt+178 bp used to map Ge epitopes against which autoantibodies are directed.

To map an epitope on Ge protein against which the autoantibodies are directed, fragments of the G6xt cDNA were prepared by digestion with the Bam restriction enzyme (FIG. 3 A. G6xt+178 bp; B. G6xt; C. G6; D. nucleotides 2581-4297; E. nucleotides 2515-4297 (nucleotide sequences correspond to FIG. 2 (SEQ ID No: I))). These fragments were ligated into expression vector pGEX2 (Pharmacia) and a fusion protein with glutathione-S-transferase was induced. Recombinant protein produced using the G6xt cDNA (FIG. 3B) did react with the patient's serum on an immunoblot (as described above). The cDNA G6 (FIG. 3C) in pMAL also produced a fusion product that reacted with the patient's serum. A construct containing nucleotides 2581 to 4297 did not react with the patient's serum (FIG. 3C). This construct did direct the production of an appropriate size fusion protein as determined by 8% SDS polyacrylamide gel electrophoresis and staining of the gel with Coomassie blue dye. A construct only 66 nucleotides longer ( nucleotides 2515 to 4297) did react with the patient's serum (FIG. 3E).

The 22 amino acids encoded by the additional 66 nucleotides encode part of the protein's putative nuclear localization region. Nuclear localization sequences are thought to consist of 2 regions consisting of basic amino acids separated by approximately I0 "spacer" amino acids. G6xt +178 bp contains the region "KTK.......KRKSKK". This differs only slightly from the reported consensus sequence (see Dingwall, C. and Laskey, R., 1991. Trends in Biochemical Sciences. 16:478-481). By comparison with the amino acid sequence of other polypeptides, this region is likely to be responsible for directing the transport of this protein from the cytoplasm, where it is produced, to the cellular nucleus.

Purification of the Ge protein

The Ge protein polypeptide can be purified using conventional methods of protein isolation known to one schooled in the art, e.g., methods including but not limited to precipitation, chromatography, immunoadsorption, or affinity techniques The polypeptide can be purified from starting material using serum from the Sjogren's syndrome patient described above; using serum from other Sjogren's syndrome patients; using the cDNAs described above; using a genomic DNA clone encoding the Ge protein, described above; using a recombinant form of these cDNAs genetically engineered into an overproducing cell line; or by making a fusion protein of the Ge protein with another recombinant protein, e.g., with a fragment of the maltose binding protein or the glutathione-S-transferase protein, similar to the ones described above. These fusion constructs may be made with the vector pMAL (New England Biolabs) or the vector pGEX2 (Pharmacia), which is then purified on affinity columns specific for the maltose binding protein or the glutathione-S-transferase protein, respectively. These procedures are an example of, but are not limiting on, the methods of the invention.

Use

The peptides of the invention may be administered to a mammal, particularly a human, in one of the following modes (e.g., orally, parenterally, transdermally, or trandsmucosally), in a sustained release formulation using a biodegradable biocompatible polymer, or by on-site delivery using micelles, gels and liposomes or by transgenic modes.

Other embodiments

The Ge polypeptide encoding DNA can be used to make recombinant protein that can be used to screen serum from patients with autoimmune disease. In the past, production of antigens to be used to screen patient's serum was a difficult, time consuming and uncertain process. This cDNA will facilitate production of recombinant protein that can be purified and used to screen sera.

The observation that autoantibodies are directed against the nuclear localization region may be a unifying concept in this field. The majority of autoantigens are nuclear in location Several of the previously described autoantigens have their nuclear localization signals contained within their (relatively large) mapped epitopes. Finally, viral proteins, such as SV40 large T antigen and adenovirus EIa, also have nuclear localization regions. Viruses enter the cell and their DNA often is incorporated into the cellular DNA where it dictates production of viral proteins. Viral proteins are made in the cellular cytoplasm (as are the cellular proteins) and some must also make their way back into the nucleus to interact with viral and cellular DNA. Because viral proteins may use the same mechanism to return to the nucleus as cellular proteins, the structure of the nuclear localization region of the viral protein may be similar to that of the cellular protein. As the individual's immune system attempts to fight the viral infection, antibodies directed against the viral proteins may be made; these antibodies may cross-react with the cellular proteins that have a similar nuclear localization region. Thus, the patient develops "autoantibodies" and has a positive test for ANA.

In as much as preventing the viral infection may prevent the development of the autoimmune disease, the nuclear localization region may prove to be very important. Vaccination of susceptible individuals with material that contains this and other nuclear localization regions may eventually prevent the infection, and the autoimmune disease, from developing.

Ge polypeptides of the invention can be used to induce tolerance to conditions characterized by the production of autoantibodies that bind to the Ge autoantigen. The tolerogenic compounds include a Ge polypeptide and a soluble non-immunogenic carrier, e.g., isologous IgG light chain, see Golan et al., 1971, *J. Exp. Med.* 137:1064, hereby incorporated by reference. DNA encoding the tolerogenic peptide can be fused to DNA encoding the protein carrier portion of the tolerogen. The DNA encoding the peptide can include additional nucleotides at one or both ends to serve as linkers for insertion into a desired restriction site. One or more copies of the DNA encoding the tolerogenic peptide of the invention may be inserted at one or more sites in the DNA encoding the carrier. Thus, the placement and number of the insertions can be precisely controlled in the construction of the fusion gene. The fusion gene, accompanied by sequences necessary for its expression, is inserted into an expression vector and used to transform cells of a suitable expression system.

The carrier molecule of a preferred embodiment is isologous (i.e., for human treatment, human) IgG. Golan et al. 1971, suora, reports that the induction of tolerence may be strongly influenced by the carrier moiety and that IgG was the most tolerogenic of a group of carriers tested.

The sequences of carrier molecules, the methods used in the synthesis of the DNA sequences, the construction of fusion genes, and the appropriate vectors and expression systems are all well known to those skilled in the art.

In other embodiments the peptides of the invention are synthesized and linked to carrier moieties by small homobifunctional or heterobifunctional cross-linking reagents. For example, peptides can be linked by the cross-linker N-succinimidyl-3-(2-pridydithio)propinate, which contains a disulfide bond. The method has been used to couple the ricin A chain to cell-reactive antibodies in the production of immunotoxic conjugates. These techniques are reviewed in Vitetta et al., 1987. *Science* 238:1098, hereby incorporated by reference.

In other embodiments non-proteinacious nonimmunogenic carrier molecules, including D-aminoglutamic acid (Katz et al., 1971. *J. Exper. Med.* 134:201), carboxymethyl cellulose (Diner et al., 1979. *J. Immunol.* 122:1986 and polyethylene glycol (Wilkinson et al., 1987. *J. Immunol.* 139:326), can be linked to the peptides of the invention.

There are known methods of inducing tolerance. See for example, Borel et al., 1988. *J. Clin. Invest.* 82:1901, hereby incorporated by reference; Jenkins et al., 1987. *J. Exp. Med.* 165:203, hereby incorporated by reference; and Quill et al., 1987, *J. of Immunol.* 138:3704, hereby incorporated by reference.

The tolerogens of the invention will generally be admixed with a non-toxic, pharmaceutically acceptable carrier substance. Administration will generally be intravenously, parenterally or subcutaneously Other embodiments are within the following claims.

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 4237
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GAAT TCG GGG CAG GTC ATC TGT CTC TCA GGA GAT GAT AGC TCC ACC TGC            49
     Asn Ser Gly Gln Val Ile Cys Leu Ser Gly Asp Asp Ser Ser Thr Cys
     1           5                   10                  15

ATT GGG ATT TGG CCA AGG AGT GAG ATT GTG GCT AGC AGT GAC TCT AGC             97
Ile Gly Ile Trp Pro Arg Ser Glu Ile Val Ala Ser Ser Asp Ser Ser
            20                  25                  30

ATT TCA AGC AAG GCC CGG GGA AGC AAC AAG GTG AAA ATT CAG CCT GTC            145
Ile Ser Ser Lys Ala Arg Gly Ser Asn Lys Val Lys Ile Gln Pro Val
```

```
                    35                          40                              45
GCC  AAG  TAT  GAC  TGG  GAA  CAG  AAG  TAC  TAC  TAT  GGC  AAC  CTG  ATT  GCT       193
Ala  Lys  Tyr  Asp  Trp  Glu  Gln  Lys  Tyr  Tyr  Tyr  Gly  Asn  Leu  Ile  Ala
     50                       55                       60

GTG  TCT  AAC  TCC  TTC  TTG  GCC  TAT  GCC  ATT  CGG  GCT  GCC  AAC  AAT  GGC       241
Val  Ser  Asn  Ser  Phe  Leu  Ala  Tyr  Ala  Ile  Arg  Ala  Ala  Asn  Asn  Gly
65                       70                       75                       80

TCT  GCC  ATG  GTG  CGG  GTG  ATC  AGC  GTC  AGC  ACT  TCG  GAG  CGG  ACC  TTG       289
Ser  Ala  Met  Val  Arg  Val  Ile  Ser  Val  Ser  Thr  Ser  Glu  Arg  Thr  Leu
               85                       90                       95

CTC  AAG  GGC  TTC  ACA  GGC  AGT  GTG  GCT  GAT  CTG  GCT  TTC  GCG  CAC  CTC       337
Leu  Lys  Gly  Phe  Thr  Gly  Ser  Val  Ala  Asp  Leu  Ala  Phe  Ala  His  Leu
               100                      105                      110

AAC  TCT  CCA  CAG  CTG  GCC  TGC  CTG  GAT  GAG  GCA  GGC  AAC  CTG  TTC  GTG       385
Asn  Ser  Pro  Gln  Leu  Ala  Cys  Leu  Asp  Glu  Ala  Gly  Asn  Leu  Phe  Val
          115                      120                      125

TGG  CGC  TTG  GCT  CTG  GTT  AAT  GGC  AAA  ATT  CAA  GAA  GAG  ATC  TTG  GTC       433
Trp  Arg  Leu  Ala  Leu  Val  Asn  Gly  Lys  Ile  Gln  Glu  Glu  Ile  Leu  Val
130                      135                      140

CAT  ATT  CGG  CAG  CCA  GAG  GGC  ACG  CCA  CTG  AAC  CAC  TTT  CGC  AGG  ATC       481
His  Ile  Arg  Gln  Pro  Glu  Gly  Thr  Pro  Leu  Asn  His  Phe  Arg  Arg  Ile
145                      150                      155                      160

ATC  TGG  TGC  CCC  TTC  ATC  CCT  GAG  GAG  AGC  GAA  GAC  TGC  TGT  GAG  GAG       529
Ile  Trp  Cys  Pro  Phe  Ile  Pro  Glu  Glu  Ser  Glu  Asp  Cys  Cys  Glu  Glu
                    165                      170                      175

AGC  AGC  CCA  ACA  GTG  GCC  CTG  CTG  CAT  GAA  GAC  CGG  GCT  GAG  GTG  TGG       577
Ser  Ser  Pro  Thr  Val  Ala  Leu  Leu  His  Glu  Asp  Arg  Ala  Glu  Val  Trp
               180                      185                      190

GAC  CTG  GAC  ATC  GTC  CGC  TCC  AGC  CAC  AGT  ACC  TGG  CCT  GTG  GAT  GTT       625
Asp  Leu  Asp  Ile  Val  Arg  Ser  Ser  His  Ser  Thr  Trp  Pro  Val  Asp  Val
          195                      200                      205

AGC  CAG  ATC  AAG  CAG  GGC  TTC  ATT  GTG  GTA  AAA  GGT  CAT  AGC  ACG  TGC       673
Ser  Gln  Ile  Lys  Gln  Gly  Phe  Ile  Val  Val  Lys  Gly  His  Ser  Thr  Cys
210                      215                      220

CTC  AGT  GAA  GGA  GCC  CTC  TCT  CCT  GAT  GGG  ACT  GTG  CTG  GCT  ACT  GCG       701
Leu  Ser  Glu  Gly  Ala  Leu  Ser  Pro  Asp  Gly  Thr  Val  Leu  Ala  Thr  Ala
225                      230                      235                      240

AGC  CAC  GAT  GGC  TAT  GTC  AAG  TTC  TGG  CAG  ATC  TAC  ATT  GAG  GGG  CAA       769
Ser  His  Asp  Gly  Tyr  Val  Lys  Phe  Trp  Gln  Ile  Tyr  Ile  Glu  Gly  Gln
                    245                      250                      255

GAT  GAG  CCA  AGG  TGT  CTG  CAC  GAG  TGG  AAA  CCT  CAT  GAT  GGG  CGG  CCC       817
Asp  Glu  Pro  Arg  Cys  Leu  His  Glu  Trp  Lys  Pro  His  Asp  Gly  Arg  Pro
               260                      265                      270

CTC  TCC  TGC  CTC  CTG  TTC  TGT  GAC  AAC  CAT  AAG  AAA  CAA  GAC  CCT  GAT       865
Leu  Ser  Cys  Leu  Leu  Phe  Cys  Asp  Asn  His  Lys  Lys  Gln  Asp  Pro  Asp
          275                      280                      285

GTC  CCT  TTC  TGG  AGG  TTC  CTT  ATT  ACT  GGT  GCT  GAC  CAG  AAC  CGA  GAG       913
Val  Pro  Phe  Trp  Arg  Phe  Leu  Ile  Thr  Gly  Ala  Asp  Gln  Asn  Arg  Glu
290                      295                      300

TTA  AAG  ATG  TGG  TGT  ACA  GTA  TCC  TGG  ACC  TGC  CTG  CAG  ACT  ATT  CGC       961
Leu  Lys  Met  Trp  Cys  Thr  Val  Ser  Trp  Thr  Cys  Leu  Gln  Thr  Ile  Arg
305                      310                      315                      320

TTC  TCC  CCA  GAT  ATC  TTC  AGC  TCA  GTG  AGT  GTG  CCC  CCT  AGC  CTC  AAG      1009
Phe  Ser  Pro  Asp  Ile  Phe  Ser  Ser  Val  Ser  Val  Pro  Pro  Ser  Leu  Lys
                    325                      330                      335

GTT  TGC  TTG  GAC  CTC  TCA  GCA  GAA  TAC  CTG  ATT  CTC  AGC  GAT  GTG  CAA      1057
Val  Cys  Leu  Asp  Leu  Ser  Ala  Glu  Tyr  Leu  Ile  Leu  Ser  Asp  Val  Gln
               340                      345                      350

CGG  AAG  GTC  CTC  TAT  GTG  ATG  GAG  CTG  CTG  CAA  AAC  CAG  GAG  GAG  GGC      1105
Arg  Lys  Val  Leu  Tyr  Val  Met  Glu  Leu  Leu  Gln  Asn  Gln  Glu  Glu  Gly
          355                      360                      365
```

-continued

| | | | | | | | | | | | | | | | |
|---|---|---|---|---|---|---|---|---|---|---|---|---|---|---|---|
| CAC | GCC | TGC | TTC | AGC | TCC | ATC | TCG | GAG | TTC | CTG | CTC | ACC | CAC | CCT | GTG | 1153 |
| His | Ala | Cys | Phe | Ser | Ser | Ile | Ser | Glu | Phe | Leu | Leu | Thr | His | Pro | Val |
| | 370 | | | | 375 | | | | | 380 | | | | | |

| CTG | AGC | TTT | GGT | ATC | CAG | GTT | GTG | AGT | CGC | TGC | CGG | CTA | CGG | CAC | ACT | 1201 |
| Leu | Ser | Phe | Gly | Ile | Gln | Val | Val | Ser | Arg | Cys | Arg | Leu | Arg | His | Thr |
| 385 | | | | | 390 | | | | | 395 | | | | | 400 |

| GAG | GTG | CTG | CCT | GCC | GAA | GAG | GAA | AAT | GAC | AGC | CTG | GGT | GCT | GAT | GGT | 1249 |
| Glu | Val | Leu | Pro | Ala | Glu | Glu | Glu | Asn | Asp | Ser | Leu | Gly | Ala | Asp | Gly |
| | | | | 405 | | | | | 410 | | | | | 415 | |

| ACC | CAT | GGA | GCC | GGT | GCC | ATG | GAG | TCT | GCG | GCC | GGT | GTG | CTC | ATC | AAG | 1297 |
| Thr | His | Gly | Ala | Gly | Ala | Met | Glu | Ser | Ala | Ala | Gly | Val | Leu | Ile | Lys |
| | | | 420 | | | | | 425 | | | | | 430 | | |

| CTC | TTT | TGT | GTG | CAT | ACT | AAG | GCA | CTG | CAA | GAT | GTG | CAG | ATC | CGC | TTC | 1345 |
| Leu | Phe | Cys | Val | His | Thr | Lys | Ala | Leu | Gln | Asp | Val | Gln | Ile | Arg | Phe |
| | | 435 | | | | 440 | | | | | 445 | | | | |

| CAG | CCA | CAG | CTG | AAC | CCT | GAT | GTG | GTG | GCC | CCA | CTG | GGG | ACC | CAC | ACT | 1393 |
| Gln | Pro | Gln | Leu | Asn | Pro | Asp | Val | Val | Ala | Pro | Leu | Gly | Thr | His | Thr |
| 450 | | | | | 455 | | | | | 460 | | | | | |

| GCC | CAC | GAG | GAC | TTC | ACA | TTT | GGA | GAG | TCT | CGG | CCC | GAA | CTG | GGC | TCT | 1441 |
| Ala | His | Glu | Asp | Phe | Thr | Phe | Gly | Glu | Ser | Arg | Pro | Glu | Leu | Gly | Ser |
| 465 | | | | | 470 | | | | | 475 | | | | | 480 |

| GAG | GGC | CTG | GGG | TCA | GCC | GCT | CAC | GGC | TCC | CAG | CCT | GAC | CTC | CGA | CGA | 1489 |
| Glu | Gly | Leu | Gly | Ser | Ala | Ala | His | Gly | Ser | Gln | Pro | Asp | Leu | Arg | Arg |
| | | | | 485 | | | | | 490 | | | | | 495 | |

| ATC | GTG | GAG | CTG | CCT | GCA | CCT | GCC | GAC | TTC | CTC | AGT | CTG | AGC | AGT | GAG | 1537 |
| Ile | Val | Glu | Leu | Pro | Ala | Pro | Ala | Asp | Phe | Leu | Ser | Leu | Ser | Ser | Glu |
| | | | 500 | | | | | 505 | | | | | 510 | | |

| ACC | AAG | CCC | AAG | TTG | ATG | ACA | CCT | GAC | GCC | TTC | ATG | ACA | CCT | AGC | GCC | 1585 |
| Thr | Lys | Pro | Lys | Leu | Met | Thr | Pro | Asp | Ala | Phe | Met | Thr | Pro | Ser | Ala |
| | | 515 | | | | | 520 | | | | | 525 | | | |

| TCC | TTG | CAG | CAG | ATC | ACT | GCC | TCT | CCC | AGC | AGC | AGC | AGC | AGC | GGT | AGC | 1633 |
| Ser | Leu | Gln | Gln | Ile | Thr | Ala | Ser | Pro | Ser | Ser | Ser | Ser | Ser | Gly | Ser |
| | 530 | | | | | 535 | | | | | 540 | | | | |

| AGC | AGC | AGC | AGC | AGT | AGC | AGC | AGC | TCC | CTT | ACA | GCT | GTG | TCT | GCC | | 1681 |
| Ser | Ser | Ser | Ser | Ser | Ser | Ser | Ser | Ser | Leu | Thr | Ala | Val | Ser | Ala |
| 545 | | | | | 550 | | | | | 555 | | | | | 560 |

| ATG | AGC | AGC | ACC | TCA | GCT | GTG | GAC | CCC | TCC | TTG | ACC | AGG | CCA | CCT | GAG | 1729 |
| Met | Ser | Ser | Thr | Ser | Ala | Val | Asp | Pro | Ser | Leu | Thr | Arg | Pro | Pro | Glu |
| | | | | 565 | | | | | 570 | | | | | 575 | |

| GAG | CTG | ACC | TTG | AGC | CCC | AAG | CTG | CAG | CTG | GAT | GGC | AGC | CTG | ACA | ATG | 1777 |
| Glu | Leu | Thr | Leu | Ser | Pro | Lys | Leu | Gln | Leu | Asp | Gly | Ser | Leu | Thr | Met |
| | | | 580 | | | | | 585 | | | | | 590 | | |

| AGC | AGC | AGT | GGC | AGC | CTT | CAG | GCA | AGC | CCG | CGT | GGC | CTC | CTG | CCT | GGC | 1825 |
| Ser | Ser | Ser | Gly | Ser | Leu | Gln | Ala | Ser | Pro | Arg | Gly | Leu | Leu | Pro | Gly |
| | | 595 | | | | | 600 | | | | | 605 | | | |

| CTG | CTC | CCA | GCC | CCA | GCT | GAC | AAA | CTG | ACT | CCC | AAG | GGG | CCG | GGC | CAG | 1873 |
| Leu | Leu | Pro | Ala | Pro | Ala | Asp | Lys | Leu | Thr | Pro | Lys | Gly | Pro | Gly | Gln |
| | 610 | | | | | 615 | | | | | 620 | | | | |

| GTG | CCT | ACT | GCC | ACC | TCT | GCA | CTG | TCC | CTG | GAG | CTG | CAG | GAA | GTG | GAG | 1921 |
| Val | Pro | Thr | Ala | Thr | Ser | Ala | Leu | Ser | Leu | Glu | Leu | Gln | Glu | Val | Glu |
| 625 | | | | | 630 | | | | | 635 | | | | | 640 |

| CCC | CTG | GGG | CTA | CCC | CAA | GCC | TCC | CCT | AGC | CGC | ACT | CGT | TCC | CCT | GAT | 1969 |
| Pro | Leu | Gly | Leu | Pro | Gln | Ala | Ser | Pro | Ser | Arg | Thr | Arg | Ser | Pro | Asp |
| | | | | 645 | | | | | 650 | | | | | 655 | |

| GTC | ATC | TCC | TCA | GCT | TCC | ACT | GAC | CTG | TCC | CAG | GAC | ATC | CCT | GAG | ATT | 2017 |
| Val | Ile | Ser | Ser | Ala | Ser | Thr | Asp | Leu | Ser | Gln | Asp | Ile | Pro | Glu | Ile |
| | | | 660 | | | | | 665 | | | | | 670 | | |

| GCA | TCT | GAG | GCC | CTG | TCC | CGT | GGT | TTT | GGC | TCC | TCT | GCA | CCA | GAG | GGC | 2065 |
| Ala | Ser | Glu | Ala | Leu | Ser | Arg | Gly | Phe | Gly | Ser | Ser | Ala | Pro | Glu | Gly |
| | | 675 | | | | | 680 | | | | | 685 | | | |

| CTT | GAG | CCA | GAC | AGT | ATG | GCT | TCA | GCC | GCC | TCG | GCA | CTG | CAC | CTG | CTG | 2113 |
| Leu | Glu | Pro | Asp | Ser | Met | Ala | Ser | Ala | Ala | Ser | Ala | Leu | His | Leu | Leu |

-continued

| | | | | | | | | | | | | | | | | |
|---|---|---|---|---|---|---|---|---|---|---|---|---|---|---|---|---|
| | | 690 | | | | | 695 | | | | | 700 | | | | |
| TCC | CCA | CGG | CCC | CGG | CCA | GGG | CCC | GAG | CTC | GGC | CCC | CAG | CTC | GGG | CTT | 2161 |
| Ser | Pro | Arg | Pro | Arg | Pro | Gly | Pro | Glu | Leu | Gly | Pro | Gln | Leu | Gly | Leu | |
| 705 | | | | | 710 | | | | | 715 | | | | | 720 | |
| GAT | GGA | GGC | CCT | GGG | GAT | GGA | GAT | CGG | CAT | AAT | ACC | CCC | TCC | CTC | CTG | 2209 |
| Asp | Gly | Gly | Pro | Gly | Asp | Gly | Asp | Arg | His | Asn | Thr | Pro | Ser | Leu | Leu | |
| | | | | 725 | | | | | 730 | | | | | 735 | | |
| GAG | GCA | GCC | TTG | ACC | CAG | GAG | GCC | TCG | ACT | CCT | GAC | AGT | CAG | GTT | TGG | 2257 |
| Glu | Ala | Ala | Leu | Thr | Gln | Glu | Ala | Ser | Thr | Pro | Asp | Ser | Gln | Val | Trp | |
| | | | 740 | | | | | 745 | | | | | 750 | | | |
| CCC | ACA | GCA | CCT | GAC | ATT | ACT | CGT | GAG | ACC | TGC | AGC | ACC | CTG | GCA | GAA | 2305 |
| Pro | Thr | Ala | Pro | Asp | Ile | Thr | Arg | Glu | Thr | Cys | Ser | Thr | Leu | Ala | Glu | |
| | | 755 | | | | | 760 | | | | | 765 | | | | |
| AGC | CCC | AGG | AAT | GGC | CTT | CAG | GAA | AAG | CAC | AAG | AGC | CTG | GCC | TTC | CAC | 2353 |
| Ser | Pro | Arg | Asn | Gly | Leu | Gln | Glu | Lys | His | Lys | Ser | Leu | Ala | Phe | His | |
| | 770 | | | | | 775 | | | | | 780 | | | | | |
| CGA | CCA | CCA | TAT | CAC | CTG | CTG | CAG | CAA | CGT | GAC | AGC | CAG | GAT | GCC | AGT | 2401 |
| Arg | Pro | Pro | Tyr | His | Leu | Leu | Gln | Gln | Arg | Asp | Ser | Gln | Asp | Ala | Ser | |
| 785 | | | | | 790 | | | | | 795 | | | | | 800 | |
| GCT | GAG | CAA | AGT | GAC | CAT | GAT | GAT | GAG | GTG | GCC | AGC | CTT | GCC | TCT | GCT | 2449 |
| Ala | Glu | Gln | Ser | Asp | His | Asp | Asp | Glu | Val | Ala | Ser | Leu | Ala | Ser | Ala | |
| | | | | 805 | | | | | 810 | | | | | 815 | | |
| TCA | GGA | GGC | TTA | CGA | CTC | GTT | TCA | CTG | GTA | CTA | CTA | CTC | CAC | CGG | TCG | 2497 |
| Ser | Gly | Gly | Leu | Arg | Leu | Val | Ser | Leu | Val | Leu | Leu | Leu | His | Arg | Ser | |
| | | | 820 | | | | | 825 | | | | | 830 | | | |
| GAA | CGG | AGA | CGA | AGT | CCT | CCG | AAT | GGC | ACC | AAA | GTT | CCT | GCT | CCA | CGG | 2545 |
| Glu | Arg | Arg | Arg | Ser | Pro | Pro | Asn | Gly | Thr | Lys | Val | Pro | Ala | Pro | Arg | |
| | | 835 | | | | | 840 | | | | | 845 | | | | |
| CTG | CCT | GCC | AAG | GAC | TGG | AAG | ACC | AAG | GGA | TCC | CCT | CGA | ACC | TCA | CCC | 2593 |
| Leu | Pro | Ala | Lys | Asp | Trp | Lys | Thr | Lys | Gly | Ser | Pro | Arg | Thr | Ser | Pro | |
| | 850 | | | | | 855 | | | | | 860 | | | | | |
| AAG | CTC | AAG | AGG | AAA | AGC | AAG | AAG | GAT | GAT | GGG | GAT | GCA | GCC | ATG | GGA | 2641 |
| Lys | Leu | Lys | Arg | Lys | Ser | Lys | Lys | Asp | Asp | Gly | Asp | Ala | Ala | Met | Gly | |
| 865 | | | | | 870 | | | | | 875 | | | | | 880 | |
| TCC | CGG | CTC | ACA | GAG | CAC | CAG | GTG | GCA | GAG | CCC | CCT | GAG | GAC | TGG | CCA | 2689 |
| Ser | Arg | Leu | Thr | Glu | His | Gln | Val | Ala | Glu | Pro | Pro | Glu | Asp | Trp | Pro | |
| | | | | 885 | | | | | 890 | | | | | 895 | | |
| GCA | CTA | ATT | TGG | CAA | CAG | CAG | AGA | GAG | CTG | GCA | GAG | CTG | CGG | CAC | AGC | 2737 |
| Ala | Leu | Ile | Trp | Gln | Gln | Gln | Arg | Glu | Leu | Ala | Glu | Leu | Arg | His | Ser | |
| | | | 900 | | | | | 905 | | | | | 910 | | | |
| CAG | GAA | GAG | CTG | CTG | CAG | CGT | CTG | TGT | ACC | CAA | CTC | GAA | GGC | CTG | CAG | 2785 |
| Gln | Glu | Glu | Leu | Leu | Gln | Arg | Leu | Cys | Thr | Gln | Leu | Glu | Gly | Leu | Gln | |
| | | 915 | | | | | 920 | | | | | 925 | | | | |
| AGC | ACA | GTC | ACA | GGC | CAC | GTA | GAA | CGT | GCC | CTT | GAG | ACT | CGG | CAC | GAG | 2833 |
| Ser | Thr | Val | Thr | Gly | His | Val | Glu | Arg | Ala | Leu | Glu | Thr | Arg | His | Glu | |
| | | 930 | | | | | 935 | | | | | 940 | | | | |
| CAG | GAA | CAG | CGG | CGG | CTG | GAG | CGA | GCA | CTG | GCT | GAG | GGG | CAG | CAG | CGG | 2881 |
| Gln | Glu | Gln | Arg | Arg | Leu | Glu | Arg | Ala | Leu | Ala | Glu | Gly | Gln | Gln | Arg | |
| 945 | | | | | 950 | | | | | 955 | | | | | 960 | |
| GGA | GGG | CAC | TGG | CAG | GAG | CAG | CTG | ACA | CAA | CAG | TTG | TCC | CAA | GCA | CTG | 2929 |
| Gly | Gly | His | Trp | Gln | Glu | Gln | Leu | Thr | Gln | Gln | Leu | Ser | Gln | Ala | Leu | |
| | | | | 965 | | | | | 970 | | | | | 975 | | |
| TCG | TCA | GCT | GTA | GCT | GGG | CGG | CTA | GAG | CGC | AGC | ATA | CGG | GAT | GAG | ATC | 2977 |
| Ser | Ser | Ala | Val | Ala | Gly | Arg | Leu | Glu | Arg | Ser | Ile | Arg | Asp | Glu | Ile | |
| | | | 980 | | | | | 985 | | | | | 990 | | | |
| AAG | AAG | ACA | GTC | CCT | CCA | TGT | GTC | TCA | AGG | AGT | CTG | GAG | GCT | ATG | GCA | 3025 |
| Lys | Lys | Thr | Val | Pro | Pro | Cys | Val | Ser | Arg | Ser | Leu | Glu | Ala | Met | Ala | |
| | | 995 | | | | | 1000 | | | | | 1005 | | | | |
| GGC | CAA | CTG | AGC | AAC | TCA | GTG | GCT | ACC | AAG | CTC | ACA | GCT | GTG | GAG | GGC | 3073 |
| Gly | Gln | Leu | Ser | Asn | Ser | Val | Ala | Thr | Lys | Leu | Thr | Ala | Val | Glu | Gly | |
| | | 1010 | | | | | 1015 | | | | | 1020 | | | | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| AGC | ATG | AAA | GAG | AAC | ATC | TCC | AAG | CTG | CTC | AAG | TCC | AAG | AAC | TTG | ACT | 3121 |
| Ser | Met | Lys | Glu | Asn | Ile | Ser | Lys | Leu | Leu | Lys | Ser | Lys | Asn | Leu | Thr |      |
| 1025 |    |     |     |     | 1030 |   |     |     |     | 1035 |   |     |     |     | 1040 |    |
| GAT | GCC | ATC | GCC | CGA | GCA | GCT | GCA | GAC | ACA | TTA | CAA | GGG | CCG | ATG | CAG | 3169 |
| Asp | Ala | Ile | Ala | Arg | Ala | Ala | Ala | Asp | Thr | Leu | Gln | Gly | Pro | Met | Gln |      |
|     |     |     |     | 1045 |   |     |     |     | 1050 |   |     |     |     | 1055 |   |      |
| GCT | GCC | TAC | CGG | GAA | GCC | TTC | CAG | AGT | GTG | GTG | CTG | CCG | GCC | TTT | GAG | 3217 |
| Ala | Ala | Tyr | Arg | Glu | Ala | Phe | Gln | Ser | Val | Val | Leu | Pro | Ala | Phe | Glu |      |
|     |     |     | 1060 |   |     |     |     | 1065 |   |     |     |     | 1070 |   |     |      |
| AAG | AGC | TGC | CAG | GCC | ATG | TTC | CAG | CAA | ATC | AAT | GAT | AGC | TTC | CGG | CTG | 3265 |
| Lys | Ser | Cys | Gln | Ala | Met | Phe | Gln | Gln | Ile | Asn | Asp | Ser | Phe | Arg | Leu |      |
|     |     | 1075 |   |     |     |     | 1080 |   |     |     |     | 1085 |   |     |     |      |
| GGG | ACA | CAG | GAA | TAC | TTG | CAG | CAG | CTA | GAA | AGC | CAC | ATG | AAG | AGC | CGG | 3313 |
| Gly | Thr | Gln | Glu | Tyr | Leu | Gln | Gln | Leu | Glu | Ser | His | Met | Lys | Ser | Arg |      |
| 1090 |    |     |     |     | 1095 |   |     |     |     | 1100 |   |     |     |     |     |      |
| AAC | GGA | CGG | GAA | CAG | GAG | GCC | AGG | GAG | CCT | GTG | CTA | GCC | CAG | CTG | CGG | 3361 |
| Asn | Gly | Arg | Glu | Gln | Glu | Ala | Arg | Glu | Pro | Val | Leu | Ala | Gln | Leu | Arg |      |
| 1105 |    |     |     |     | 1110 |   |     |     |     | 1115 |   |     |     |     | 1120 |    |
| GGC | CTG | GTC | AGC | ACA | CTG | CAG | AGT | GCC | ACT | GAG | CAG | ATG | CAG | CCA | CCG | 3409 |
| Gly | Leu | Val | Ser | Thr | Leu | Gln | Ser | Ala | Thr | Glu | Gln | Met | Gln | Pro | Pro |      |
|     |     |     |     | 1125 |   |     |     |     | 1130 |   |     |     |     | 1135 |   |      |
| TGG | CCG | GCA | GTG | TTC | GTG | CTG | AGG | TGC | AGC | ACC | AGC | TGC | ATG | TGG | CTG | 3457 |
| Trp | Pro | Ala | Val | Phe | Val | Leu | Arg | Cys | Ser | Thr | Ser | Cys | Met | Trp | Leu |      |
|     |     |     |     | 1140 |   |     |     |     | 1145 |   |     |     |     | 1150 |   |      |
| TGG | GCA | GCC | TGC | AGG | AGT | CCA | TTT | TAG | CAC | AGG | TAC | AGC | GCA | TCG | TTA | 3505 |
| Trp | Ala | Ala | Cys | Arg | Ser | Pro | Phe |     | His | Arg | Tyr | Ser | Ala | Ser | Leu |      |
|     |     |     | 1155 |   |     |     |     |     | 1160 |   |     |     |     | 1165 |   |      |
| AGG | GTG | AGG | TGAGTGTGGC | GCTCAAGGAG | CAGCAGTCTG | CCCACCTTGA |     |     |     |     |     |     |     |     |     | 3554 |
| Arg | Val | Arg |     |     |     |     |     |     |     |     |     |     |     |     |     |      |
|     |     | 1170 |   |     |     |     |     |     |     |     |     |     |     |     |     |      |

| | | | | | |
|---|---|---|---|---|---|
| CTGCCAGGCC | CAGCAAGCCC | ATATCCTGCA | GCTGCTGCAG | CAGGGCCACC | CTCAATCAGG | 3614 |
| CCTTCCAGCA | GGCGCTGACA | GCTGCTGACC | TGAACCTGGT | GCTGTATGTG | TGTGAAACTG | 3674 |
| TGGACCCAGC | CCAGGTTTTT | GGGCAGCCAC | CCTGCCCGCT | CTCCCAGCCT | GTGCTCCTTT | 3734 |
| CCCTCATCCA | GCAGCTGGCA | TCTGACTTGG | CACTCGAACT | GACCTCAAGC | TCAGCTACCT | 3794 |
| GGAAGAGGCC | GTGATGCACC | TGGACCACAG | TGACCCCATC | ACTCGGGACC | ACATGGGCTC | 3854 |
| CGTTATGGCC | CAGGTGCGCC | AAAAGCTTTT | TCAGTTCCTG | CAGGCTGAGC | CACACAACTC | 3914 |
| ACTTGGCAAA | GCAGCTCGGC | GTCTCAGCCT | CATGCTGCAT | GGCCTCGTGA | CCCCCAGCCT | 3974 |
| CCCTTAGCTG | CTAAGCCTGC | CTTGCCCAGG | GGTGGGATGG | CACTGAAGGC | CAGCAGACAG | 4034 |
| GCCTAGGCTG | GGCAGGGTC | ACGGCTGGCC | TTTACCTGCT | CAGGCCTGGT | AGTCAGAAGG | 4094 |
| TTTAGCTGGG | CCCAGGGCAG | GTATTGCGCC | TGCTTGGGTT | CTGCCATGCC | TGGAGCATGA | 4154 |
| CCCTGAGATC | GTGACACCAC | TTGAGTGGAA | TTTTCCATGT | TCCTTTTTAG | GTGTAATTTG | 4214 |
| GATCTTTTTG | TTTTGAAAAA | CAT |     |     |     | 4237 |

What is claimed is:
1. A substantially pure preparation of a Ge protein polypeptide.
2. The polypeptide of claim 1 wherein said polypeptide has an apparent molecular weight of 170 kilodaltons when derived from HeLa cells.

* * * * *

UNITED STATES PATENT AND TRADEMARK OFFICE
CERTIFICATE OF CORRECTION

PATENT NO. : 5,272,256

DATED : December 21, 1993

INVENTOR(S) : Donald B. Bloch

It is certified that error appears in the above-indentified patent and that said Letters Patent is hereby corrected as shown below:

In Column 1, line 1, insert the following: "This invention was made with Government support under Contract #A R01866 awarded by the National Institutes of Health. The Government has certain rights in this invention."

Column 1, line 61, replace "suora" with --supra--;

Column 3, line 42, after "thereof", add a period;

Column 4, line 59, after "analysis", add a period;

Column 6, line 55, after "substrate", add a period;

Column 8, line 14, replace "Two autoradiography." with --Two radiolabeled bands (170 kD and 70 kD) were detected by autoradiography.--;

Column 8, line 33, after "milk", insert a period;

Column 8, line 57, replace "Polyacrilamide" with --Polyacrylamide--;

Column 9, line 34, replace "32411" with --3241--;

Column 9, line 51, replace "I78" with --178--;

Column 9, line 56, replace "Bam" with --BamHI--;

Column 10, line 11, replace "I0" with --10--;

UNITED STATES PATENT AND TRADEMARK OFFICE
CERTIFICATE OF CORRECTION

PATENT NO. : 5,272,256
DATED : December 21, 1993
INVENTOR(S) : Donald B. Bloch

It is certified that error appears in the above-indentified patent and that said Letters Patent is hereby corrected as shown below:

Column 10, line 68, after "location", insert a period;

Column 11, line 4, replace "EIa", with --Ela--;

Column 12, line 7, replace "suora", with --supra--;

Column 12, line 26, replace "proteinacious" with --proteinaceous--.

Signed and Sealed this

Fourteenth Day of June, 1994

Attest:

BRUCE LEHMAN

Attesting Officer *Commissioner of Patents and Trademarks*